United States Patent
Blackmon

(10) Patent No.: US 11,737,757 B2
(45) Date of Patent: Aug. 29, 2023

(54) ENDOLUMINAL ANASTOMOSIS AND TISSUE CLOSURE DEVICES

(71) Applicant: Mayo Foundation for Medical Education and Research, Rochester, MN (US)

(72) Inventor: Shanda Blackmon, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 419 days.

(21) Appl. No.: 16/985,967

(22) Filed: Aug. 5, 2020

(65) Prior Publication Data
US 2020/0360020 A1   Nov. 19, 2020

Related U.S. Application Data

(62) Division of application No. 15/750,909, filed as application No. PCT/US2016/041700 on Jul. 11, 2016, now Pat. No. 10,765,433.

(Continued)

(51) Int. Cl.
*A61F 2/04*   (2013.01)
*A61B 17/11*   (2006.01)
(Continued)

(52) U.S. Cl.
CPC ...... *A61B 17/1114* (2013.01); *A61B 17/0057* (2013.01); *A61B 17/0401* (2013.01);
(Continued)

(58) Field of Classification Search
CPC ......... A61B 17/00; A61B 17/04; A61B 17/11; A61B 17/1114; A61B 17/0401;
(Continued)

(56) References Cited

U.S. PATENT DOCUMENTS

| 5,290,295 A | 3/1994 | Querals et al. |
| 2003/0040808 A1 | 2/2003 | Stack et al. |

(Continued)

FOREIGN PATENT DOCUMENTS

| EP | 2346411 | 10/2013 |
| EP | 2316346 | 12/2017 |
| WO | WO 2007/136468 | 11/2007 |

OTHER PUBLICATIONS

European Supplementary Search Report in Application No. 16835585.7 dated Mar. 13, 2019, 316 pages.

(Continued)

*Primary Examiner* — Vi X Nguyen
(74) *Attorney, Agent, or Firm* — Fish & Richardson P.C.

(57) ABSTRACT

Multiple endoscopic devices and methods for closing perforations and/or creating anastomoses in tissue are described. For example, this document provides devices and methods for performing esophagogastric anastomoses and for closing esophageal perforations in a minimally invasive fashion. The devices and methods provided herein can also be used for, without limitation, colorectal anastomoses, any bowel anastomosis, gastric bypass anastomoses, and broader vessel anastomoses.

11 Claims, 9 Drawing Sheets

Related U.S. Application Data

(60) Provisional application No. 62/202,447, filed on Aug. 7, 2015.

(51) Int. Cl.
*A61B 17/04* (2006.01)
*A61B 17/00* (2006.01)
*A61B 90/30* (2016.01)
*A61B 90/00* (2016.01)
*A61B 17/34* (2006.01)
*A61F 5/00* (2006.01)

(52) U.S. Cl.
CPC ...... *A61B 17/0469* (2013.01); *A61B 17/0487* (2013.01); *A61B 17/3468* (2013.01); *A61B 2017/0034* (2013.01); *A61B 2017/00575* (2013.01); *A61B 2017/00672* (2013.01); *A61B 2017/00818* (2013.01); *A61B 2017/00827* (2013.01); *A61B 2017/00907* (2013.01); *A61B 2017/0409* (2013.01); *A61B 2017/0417* (2013.01); *A61B 2017/0464* (2013.01); *A61B 2017/0474* (2013.01); *A61B 2017/0475* (2013.01); *A61B 2017/0488* (2013.01); *A61B 2017/1132* (2013.01); *A61B 2017/345* (2013.01); *A61B 2090/0807* (2016.02); *A61B 2090/309* (2016.02); *A61F 5/0076* (2013.01)

(58) Field of Classification Search
CPC ............ A61B 17/0057; A61B 17/0469; A61B 17/0487; A61B 17/3468; A61B 2017/0417; A61B 2017/0409; A61B 2017/0464; A61B 2017/0474
See application file for complete search history.

(56) References Cited

U.S. PATENT DOCUMENTS

| | | | |
|---|---|---|---|
| 2004/0092892 A1* | 5/2004 | Kagan | A61B 17/0401 604/270 |
| 2004/0107004 A1 | 6/2004 | Levine et al. | |
| 2007/0010832 A1 | 1/2007 | Manzo | |
| 2007/0112437 A1 | 5/2007 | Shank | |
| 2007/0276409 A1 | 11/2007 | Ortiz et al. | |
| 2008/0051631 A1 | 2/2008 | Dejima et al. | |
| 2009/0204147 A1 | 8/2009 | Rahmani | |
| 2009/0227828 A1* | 9/2009 | Swain | A61B 17/1114 600/12 |
| 2010/0094248 A1 | 4/2010 | Nguyen et al. | |
| 2011/0306992 A1 | 12/2011 | Darois et al. | |
| 2015/0142022 A1 | 5/2015 | George et al. | |

OTHER PUBLICATIONS

Extended European Search Report in European Application No. 16835585.7 dated Aug. 1, 2019.
PCT International Preliminary Report on Patentability in International Appln. No. PCT/US2016/041700, dated Feb. 13, 2018, 9 pages.
PCT International Search Report and Written Opinion in International Appln. No. PCT/US2016/041700, dated Nov. 18, 2016, 16 pages.
Blackmon et al., "Propensity-matched analysis of three techniques for intrathoracic esophagogastric anastomosis," Ann. Thorac. Surgery, May 2007, 83(5):1805-1813.

* cited by examiner

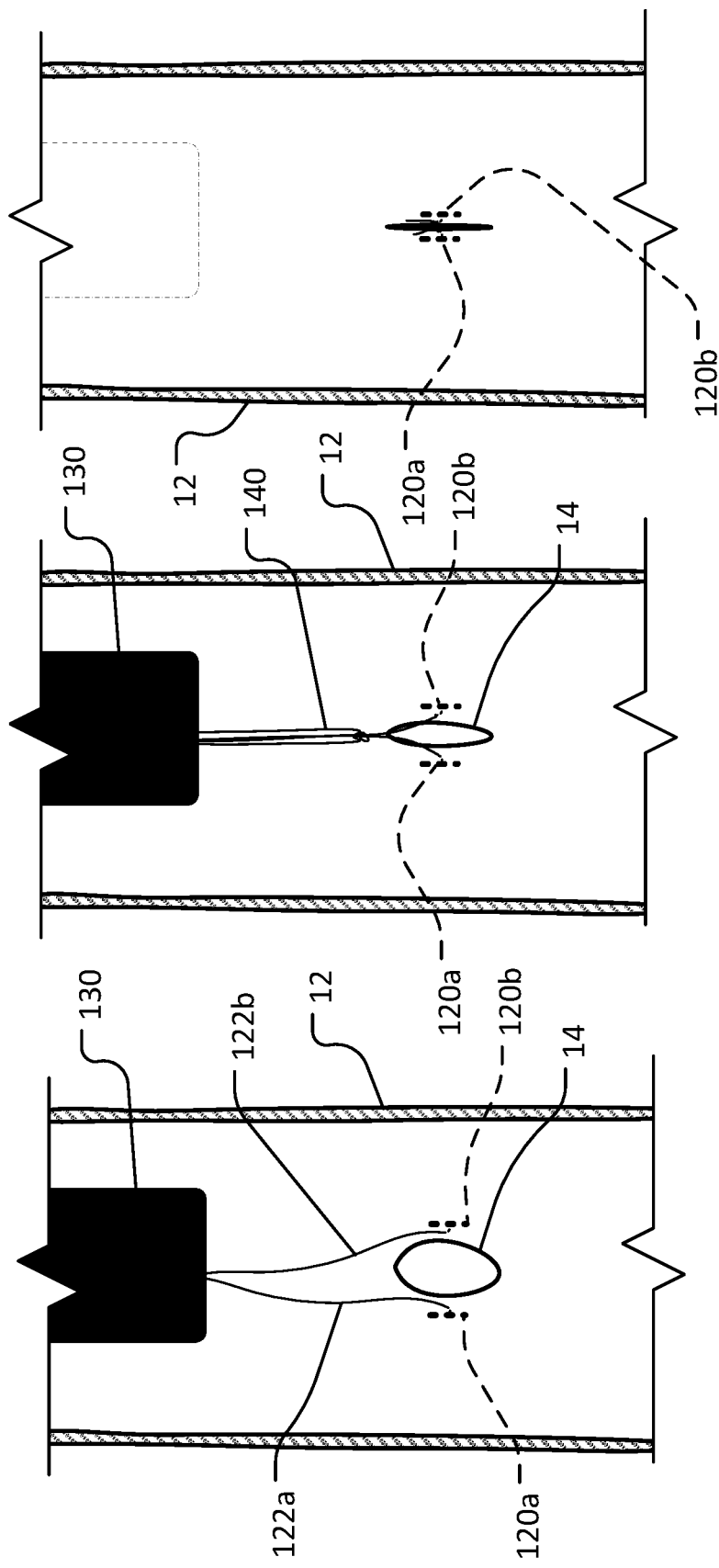

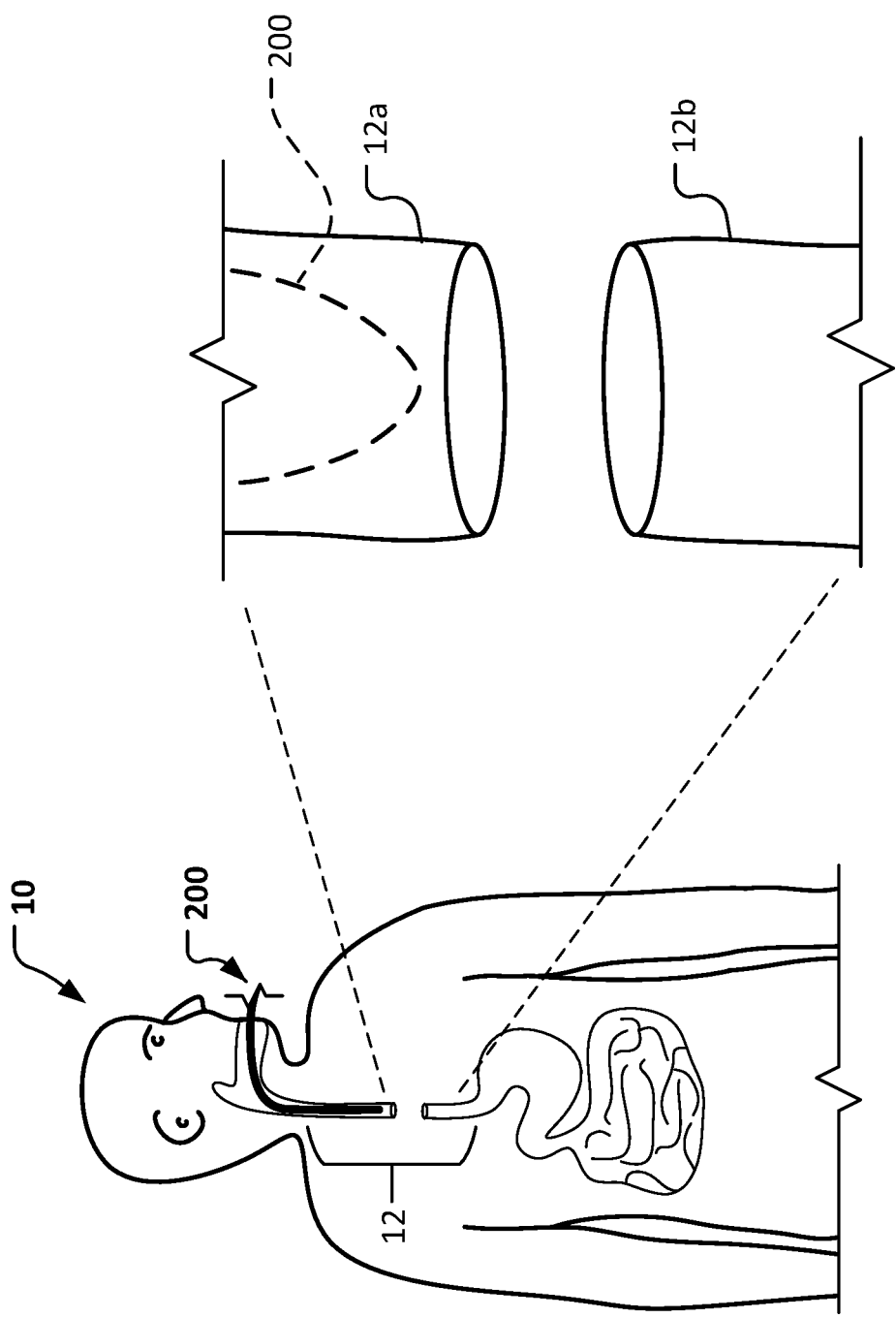

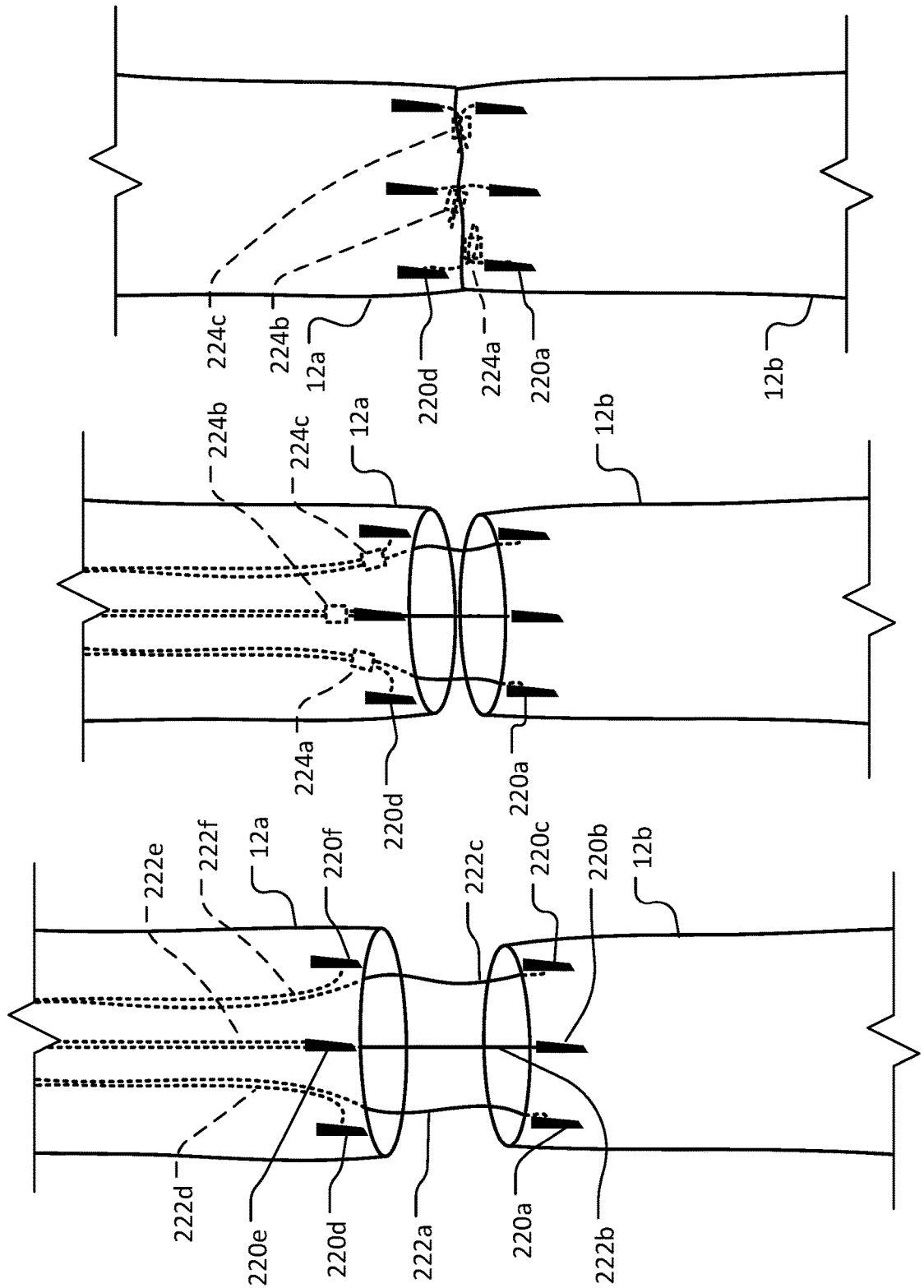

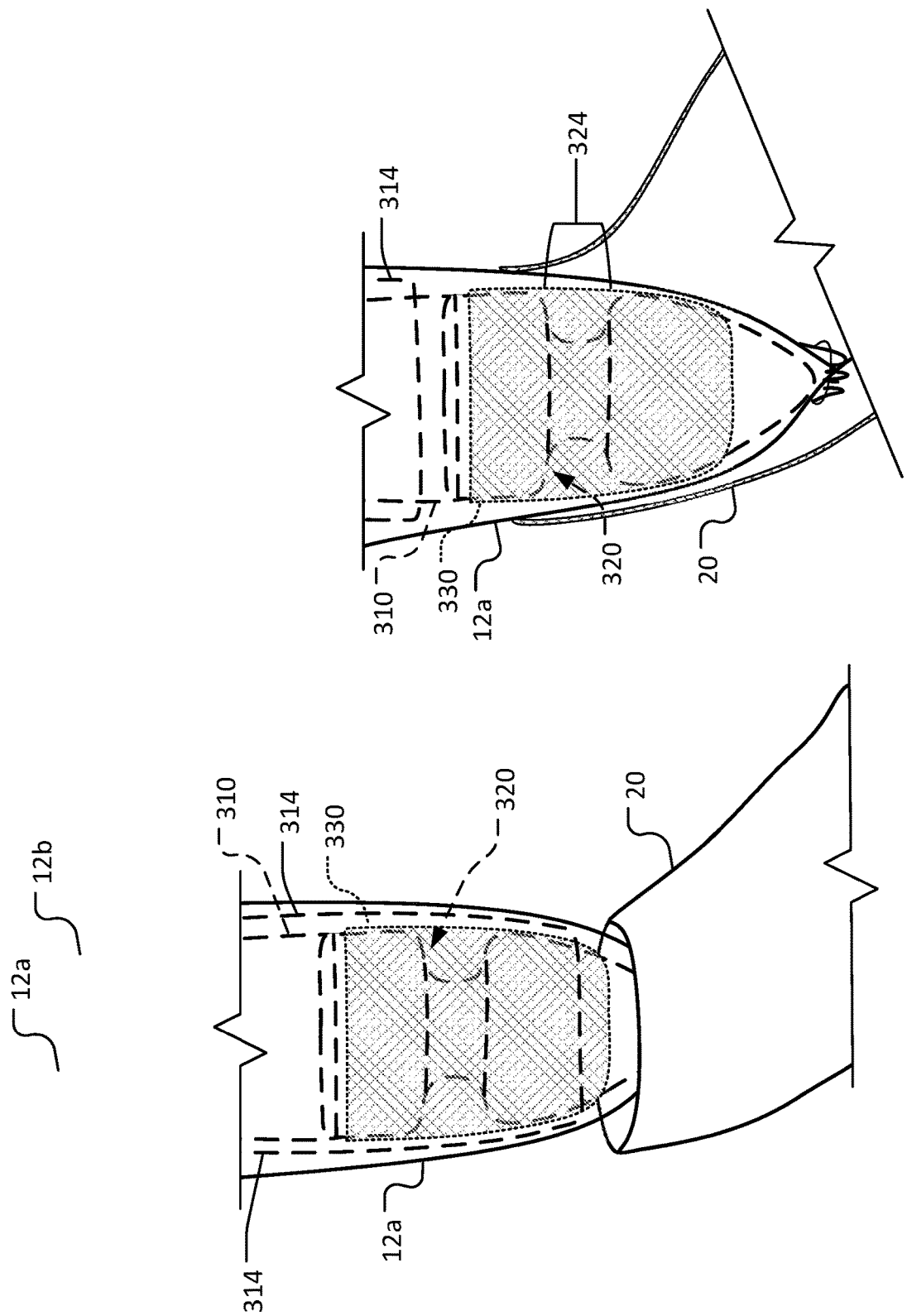

ENDOLUMINAL ANASTOMOSIS AND TISSUE CLOSURE DEVICES

CROSS REFERENCE TO RELATED APPLICATIONS

This application is a divisional of U.S. application Ser. No. 15/750,909, filed Feb. 7, 2018, which is a National Stage application under 35 U.S.C. § 371 of International Application No. PCT/US2016/041700, having an International Filing Date of Jul. 11, 2016, which claims the benefit of U.S. Provisional Ser. No. 62/202,447 filed Aug. 7, 2015. The disclosure of the prior applications are considered part of and are incorporated by reference in the disclosure of this application.

BACKGROUND

1. Technical Field

This document relates to devices and methods for closing perforations and/or creating anastomoses in tissue. For example, this document relates to devices and methods for performing esophagogastric anastomoses and for closing esophageal perforations in a minimally invasive fashion.

2. Background Information

An estimated 14,500 patients are diagnosed with esophageal cancer in the United States every year. The standard of care for patients with localized disease is resection. Although mortality rates in esophageal cancer patients undergoing esophagectomy appear to be decreasing, morbidity is still significant. Anastomotic complications have a negative effect on patient survival. Postoperative leak, dysphagia, and stricture may be indicators of the quality of an anastomosis.

The current standard of care for patients undergoing esophagectomy includes the performance of an intrathoracic esophagogastric anastomosis procedure. There are three conventional intrathoracic methods for performing such an esophagogastric anastomosis. First is the side-to-side stapled esophagogastric anastomosis. Second is the circular-stapled esophagogastric anastomosis technique. Third is the hand-sewn esophagogastric anastomosis technique. Each of these techniques is surgically invasive. Hence, a need exists for a minimally invasive esophagogastric anastomosis technique.

SUMMARY

This document provides devices and methods for closing perforations and/or creating anastomoses in tissue. For example, this document provides devices and methods for performing esophagogastric anastomoses and for closing esophageal perforations in a minimally invasive fashion. The devices and methods provided herein can also be used for, without limitation, colorectal anastomoses, any bowel anastomosis, gastric bypass anastomoses, and broader vessel anastomoses.

In one implementation, an endoscopic anastomosis device includes an endoscope with a plurality of working channels therethrough, a plurality of T-fasteners, and a plurality of sutures. Each T-fastener of the plurality of T-fasteners is slidably disposable within a working channel of the plurality of working channels. Each T-fastener of the plurality of T-fasteners has a suture of the plurality of sutures attached thereto. Distal end portions of each working channel of the plurality of working channels are configured to direct T-fasteners to emerge at least somewhat laterally from a distal tip portion of the endoscope.

Such an endoscopic anastomosis device may optionally include one or more of the following features. The distal tip portion of the endoscope may comprise a tapered leading end. The device may further comprise one or more pusher catheters that are slidably disposable within each working channel of the plurality of working channels. Each T-fastener of the plurality of T-fasteners may have a beveled tip configured for puncturing tissue. Distal end portions of each working channel of the plurality of working channels may be configured to direct T-fasteners to emerge laterally at an angle from between about 45 degrees to about 90 degrees in relation to a longitudinal axis of the endoscope.

In another implementation, a method of endoscopically creating an anastomosis between two body conduits of a patient includes deploying an endoscope anastomosis device within the patient such that the endoscope anastomosis device is within an interior of each body conduit of the two body conduits, ejecting a first grouping of T-fasteners from at least some working channels of the plurality of working channels, ejecting a second grouping of T-fasteners from at least some working channels of the plurality of working channels, and cinching individual T-fasteners of the first grouping of T-fasteners together with respective individual T-fasteners of the second grouping of T-fasteners so as to draw the first body conduit into contact with the second body conduit. The endoscope anastomosis device includes an endoscope with a plurality of working channels therethrough; a plurality of T-fasteners, each T-fastener of the plurality of T-fasteners being slidably disposable within a working channel of the plurality of working channels; and a plurality of sutures. Each T-fastener of the plurality of T-fasteners has a suture of the plurality of sutures attached thereto. Distal end portions of each working channel of the plurality of working channels are configured to direct T-fasteners to emerge at least somewhat laterally from a distal tip portion of the endoscope. The ejecting the first grouping of T-fasteners causes the first grouping of T-fasteners to puncture through a first body conduit of the two body conduits. The ejecting the second grouping of T-fasteners causes the second grouping of T-fasteners to puncture through a second body conduit of the two body conduits.

Such a method of endoscopically creating an anastomosis between two body conduits of a patient may optionally include one or more of the following features. The distal tip portion of the endoscope may include a tapered leading end. The ejecting the first grouping of T-fasteners may involve pushing the first grouping of T-fasteners out from the at least some working channels of the plurality of working channels. The ejecting the second grouping of T-fasteners may involve pushing the second grouping of T-fasteners out from the at least some working channels of the plurality of working channels. Each T-fastener of the plurality of T-fasteners may have a beveled tip configured for puncturing tissue. Distal end portions of each working channel of the plurality of working channels may be configured to direct T-fasteners to emerge laterally at an angle from between about 45 degrees to about 90 degrees in relation to a longitudinal axis of the endoscope. The cinching may be performed using suture knots and a suture knot pusher device. The cinching may be performed using suture closure clip devices. The two body conduits may be portions of an esophagus.

In another implementation, a method of closing an opening in a body conduit of a patient includes deploying an endoscope device within the patient such that the endoscope device is within an interior of the body conduit and such that a distal tip portion of the endoscope is proximate to the opening; ejecting a first T-fastener away from the endoscope such that the first T-fastener emerges at least somewhat laterally away from a longitudinal axis of the endoscope, and such that the first T-fastener proceeds through a wall of the body conduit adjacent to the opening; ejecting a second T-fastener away from the endoscope such that the second T-fastener emerges at least somewhat laterally away from the longitudinal axis of the endoscope, and such that the second T-fastener proceeds through the wall of the body conduit adjacent to the opening and generally on an opposite side of the opening in comparison to the first T-fastener; and cinching a first suture that is attached to the first T-fastener with a second suture that is attached to the second T-fastener so as to draw the first T-fastener and the second T-fastener towards each other and to thereby at least partly close the opening.

Such a method of closing an opening in a body conduit of a patient may optionally include one or more of the following features. An overtube may be slidably disposed within a working channel of the endoscope, and at least one of the first T-fastener or the second T-fastener may be ejected from the overtube. The overtube may be used to puncture the wall of the body conduit to create one or more incisions through which least one of the first T-fastener or the second T-fastener proceed. The body conduit may be an esophagus.

In another implementation, a system for creating an anastomosis includes a bougie, an obturator extending from a distal end of the bougie, a stent releasably disposable about at least a portion of the obturator, a sheath that is slidably engageable with the bougie, and a plurality of T-fasteners. The sheath includes a distal end portion configured for covering at least a portion of the stent while the stent is disposed about the obturator. The obturator includes a portion having an outer diameter relief area. Each of the plurality of T-fasteners are configured to pass through a wall of the stent. A portion of each of the plurality of T-fasteners are sized to fit within the portion having an outer diameter relief area.

Such a system for creating an anastomosis may optionally include one or more of the following features. The stent may be bioresorbable, biodegradable, or bioabsorbable. The obturator may include one or more indicator lights positioned to indicate a location of the portion having an outer diameter relief area.

In another implementation, a method of creating an anastomosis in a patient includes: (a) installing at least a portion of a bougie within an obturator extending from a distal end of the bougie into a first body conduit of the patient (a stent is releasably disposed about at least a portion of the obturator), (b) installing an end portion of the first body conduit into engagement with a second body tissue structure of the patient, (c) sliding a sheath (the sheath is slidably engaged with the bougie and covers at least a portion of the stent) proximally in relation to the bougie so that the stent is no longer covered by the sheath, (d) installing a plurality of T-fasteners, and (e) removing the bougie and obturator from the patient while leaving the stent that is attached to the first body conduit and the second body tissue structure within the patient. The portion of the obturator includes an outer diameter relief area. At least some T-fasteners of the plurality of T-fasteners extend through each of: (i) a wall of the first body conduit, (ii) a wall of the second body tissue structure, (iii) a wall of the stent, and into the outer diameter relief area.

Such a method of creating an anastomosis in a patient may optionally include one or more of the following features. The first body conduit may be an esophagus and the second body tissue structure may be a stomach. The first body conduit and the second body tissue structure may be parts of the patient's vasculature. The first body conduit and the second body tissue structure may be parts of the patient's lower GI tract.

Particular embodiments of the subject matter described in this document can be implemented to realize one or more of the following advantages. In some embodiments of the devices and methods provided herein, a minimally invasive esophagogastric anastomosis procedure can be performed. Such minimally invasive techniques can reduce recovery times, patient discomfort, and treatment costs. Additionally, some embodiments the devices and methods provided herein can also be used to close esophageal perforations, tears, and other types of openings in a minimally invasive fashion.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims. While this specification contains many specific implementation details, these should not be construed as limitations on the scope of any invention or of what may be claimed, but rather as descriptions of features that may be included in one or more particular embodiments.

DESCRIPTION OF THE DRAWINGS

FIGS. 2-4 are a series of illustrations showing steps of the process of closing the esophageal perforation using the devices and methods of FIGS. 1A and 1B in accordance with some embodiments provided herein.

FIGS. 5A and 5B illustrate a patient undergoing an example minimally invasive procedure to create an esophagogastric anastomosis using an endoscopic T-fastener anastomosis device in accordance with some embodiments provided herein.

FIGS. 6-12 are a series of illustrations showing steps of the process of creating the esophagogastric anastomosis using the devices and methods of FIGS. 5A and 5B in accordance with some embodiments provided herein.

FIGS. 14-17 are a series of illustrations showing steps of the process of creating the esophagogastric anastomosis using the devices and methods of FIGS. 13A and 13B in accordance with some embodiments provided herein.

Like reference numbers represent corresponding parts throughout.

DETAILED DESCRIPTION

This document provides devices and methods for closing perforations and/or creating anastomoses in tissue. For example, this document provides devices and methods for performing esophagogastric anastomoses and for closing esophageal perforations in a minimally invasive fashion. The devices and methods provided herein may also be used to treat other conditions, and to treat other areas of the body in addition to the esophagus. For example, the devices and methods provided herein may be used to create anastomoses or close openings in the lower GI tract, vasculature, and respiratory system, to provide some additional examples. The devices and methods provided herein may also be used for gastric bypass anastomoses and other like procedures.

Figures 1A, 1B:
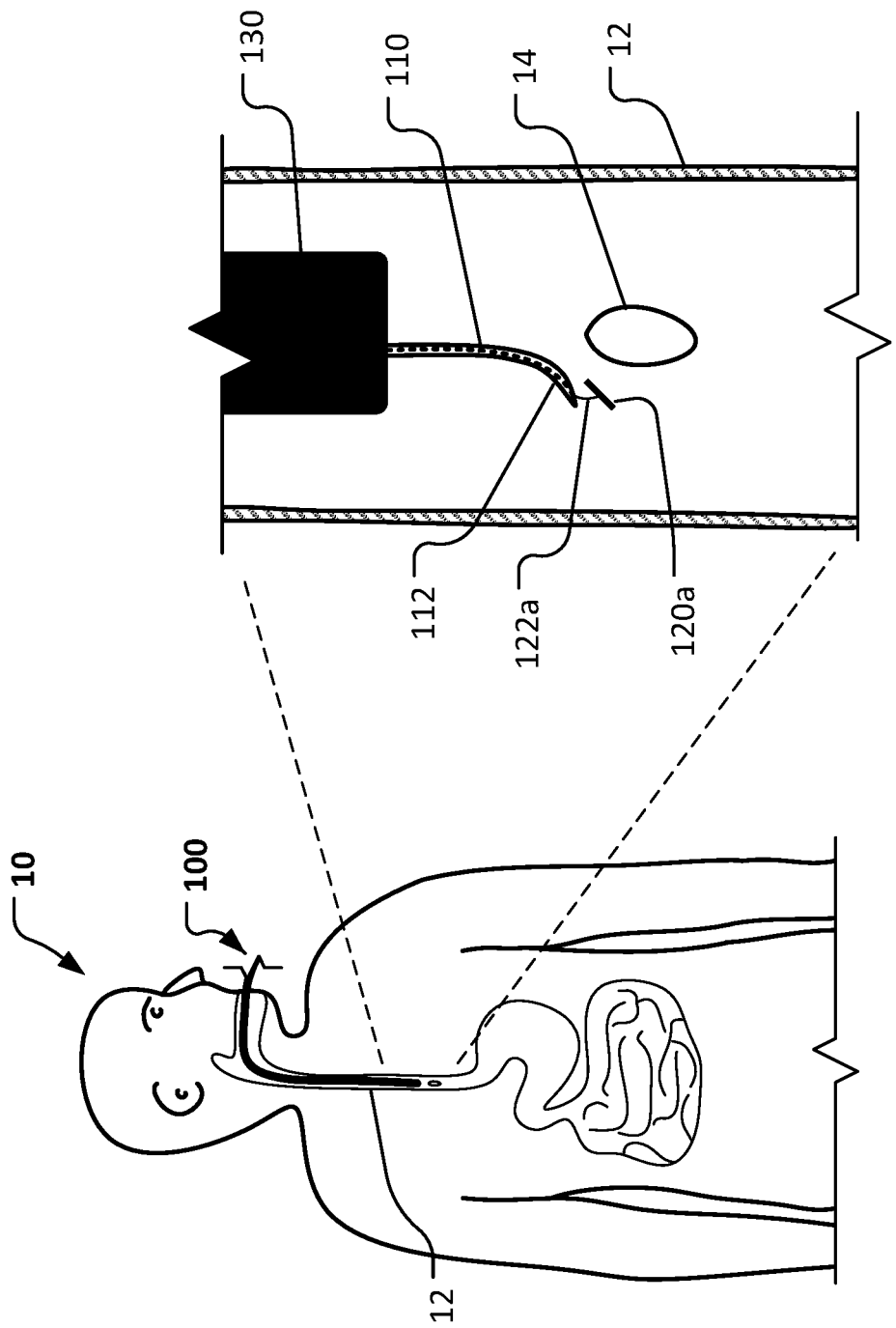
FIGS. 1A and 1B illustrate a patient undergoing a minimally invasive procedure to close an esophageal opening using an endoscopic T-fastener tissue closure device in accordance with some embodiments provided herein.

Referring to the example of FIGS. 1A and 1B, a human patient 10 can receive a treatment to close an esophageal opening 14 using an endoscopic T-fastener tissue closure device 100 in accordance with some embodiments provided herein. In the depicted embodiment, tissue closure device 100 includes an overtube 110 through which one or more T-fasteners 120a that are attached to a suture 122a can be deployed. Overtube 110 is slidably disposed within a channel of an endoscope 130.

Endoscope 130 can be inserted within esophagus 12 of patient 10. Endoscope 130 can then be navigated within esophagus 12 so that the distal end of endoscope 130 is positioned in a desired proximity to opening 14. In the depicted embodiment, overtube 110 is then expressed from endoscope 130 in preparation for installing T-fastener 120.

In some embodiments, overtube 110 has a distal tip portion 112 that is configured for puncturing through esophagus 12. For example, in the depicted embodiment distal tip portion 112 of overtube 110 is beveled to create a sharp tip for puncturing through esophagus 12. In addition, in the depicted embodiment distal tip portion 112 is flexibly radiused so that the tip of distal tip portion 112 is oriented at a steep angle in relation to esophagus 12, thereby facilitating puncture of distal tip portion 112 through esophagus 12.

In alternative embodiments, T-fastener 120a itself is the element that punctures through esophagus 12. In some such embodiments, T-fastener 120a is configured with a sharp leading end that facilitates puncture of T-fastener 120a through esophagus 12. In some embodiments, an overtube (such as, but not limited to, overtube 110) is used to orient T-fastener 120a in relation to esophagus 12 so that T-fastener 120a can puncture through esophagus 12. In some embodiments, rather than using an overtube, endoscope 130 may include one or more working channels that orient T-fastener 120a in relation to esophagus 12 so that T-fastener 120a can puncture through esophagus 12 (e.g., refer to FIG. 6).

In some embodiments, T-fastener 120a is pushed to emerge (or eject) from overtube 110 or endoscope 130 using a pusher catheter (not shown). In some embodiments, T-fastener 120a is pushed to emerge from overtube 110 or endoscope 130 using a lever mechanism as known in the art of endoscopic instruments.

After puncturing esophagus 12, T-fastener 120a is positioned on the exterior wall of esophagus 12. Suture 122a, being previously attached to T-fastener 120a, extends from T-fastener 120a, through overtube 110 and endoscope 130, and terminates at a free end that is external to patient 10 (through the mouth).

Referring also to FIG. 2, T-fastener 120a is shown installed adjacent to opening 14. In addition, a second T-fastener 120b is shown installed adjacent to opening 14 generally opposite to T-fastener 120a. T-fastener 120b can be installed using any of the techniques described above in relation to T-fastener 120a.

In some embodiments, T-fastener 120b is deployed from the same overtube 110 or working channel of endoscope 130 as T-fastener 120a was deployed from. In some embodiments, T-fastener 120b is deployed from a different overtube 110 or different working channel of endoscope 130 as T-fastener 120a was deployed from.

A suture 122b is attached to T-fastener 120b. In a manner analogous to suture 122a, in some embodiments suture 122b extends from T-fastener 120b, through overtube 110 and/or endoscope 130, and terminates at a free end that is external to patient 10 (i.e., through the mouth).

While in the depicted example implementation, opening 14 is closeable using two T-fasteners 120a-b, it should be understood that, using the inventive concepts provided herein, in some implementations more than two T-fasteners 120a-b can be installed to close an opening. For instance, larger openings may require more than two T-fasteners 120a-b. In addition, irregularly shaped openings may require more than two T-fasteners 120a-b. Further, other types of implementations may require more than two T-fasteners 120a-b. All such implementations are envisioned within the scope of this disclosure, and the inventive concepts provided herein can be applied to provide effective, advantageous, and novel treatments for such implementations.

Referring to FIGS. 3 and 4, with T-fasteners 120a-b installed on opposite sides of opening 14, then sutures 122a-b can be cinched tightly together to close opening 14. Thereafter, sutures 122a-b can be trimmed and the unattached portions can be withdrawn from esophagus 12, along with endoscope 130 and any other associated instruments.

In the depicted implementation, a knot pusher 140 is being used to cinch sutures 122a-b snugly together. In the depicted implementation, knot pusher 140 is deployed down a working channel of endoscope 130 (i.e., the same working channel that sutures 122a-b reside in). Alternatively, in some implementations endoscope 130 is withdrawn after placement of T-fasteners 120a-b, but prior to cinching sutures 122a-b. In such a case, knot pusher 140 can be deployed down esophagus 12 without being confined within endoscope 130. Knot pusher 140 can be used to tighten multiple knots between sutures 122a-b, to thereby securely and durably close opening 14.

In some embodiments, a suture closure clip device can be used on sutures 122a-b to cinch T-fasteners 120a-b together, as an alternative to tying knots in sutures 122a-b. In some such embodiments, the suture closure clip device can be pushed along sutures 122a-b and towards T-fasteners 120a-b and then used to snug T-fasteners 120a-b close together. Alternatively, in some embodiments the suture closure clip device can be installed around sutures 122a-b near opening 14 and then clamped tightly onto sutures 122a-b after sutures 122a-b are pulled tight to draw T-fasteners 120 a-b together.

Referring to FIGS. 5A and 5B, in this depiction patient 10 has had an esophagectomy. Accordingly, patient 10 is receiving a minimally invasive treatment to create an anastomosis between an esophagus end portion 12a and an esophagus end portion 12b using an endoscopic anastomosis device 200 in accordance with some embodiments provided herein.

Figure 6:
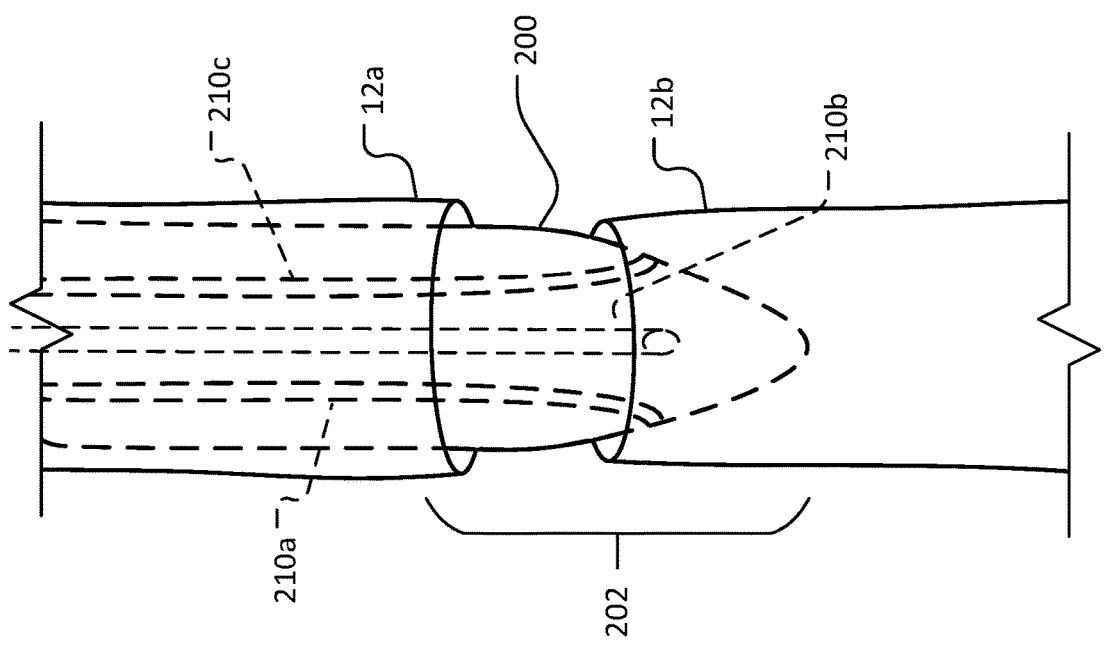

Referring also to FIG. 6, endoscopic anastomosis device 200 includes a distal tip portion 202 with a tapered leading end. The tapered leading end of distal tip portion 202 can be advantageously used to gain access within esophagus end portion 12b, and to atraumatically be advanced within esophagus 12 in general.

Endoscopic anastomosis device 200 also includes one or more working channels, such as channels 210a, 210b, and 210c. In the depicted embodiment, only three channels 210a, 210b, and 210c are shown for ease of understanding. However, it should be understood that the working channels will be distributed around the circumference of distal tip portion 202. In general, while it is not a requirement, the working channels will be distributed around the circumference of distal tip portion 202 in even angular increments. For example, when ten (10) working channels are included, the working channels may be distributed at increments of about 36° between each other so as to evenly distribute the working channels around the circumference of distal tip portion 202 in even angular increments.

In some embodiments, ten working channels are included. Alternatively, in some embodiments four, five, six, seven, eight, nine, eleven, twelve, thirteen, fourteen, fifteen, sixteen, seventeen, eighteen, nineteen, twenty, or more than twenty working channels are included.

In some embodiments, the ends of channels 210a, 210b, and 210c at distal tip portion 202 are curved so as to direct T-fasteners to emerge (i.e., eject) laterally from endoscopic anastomosis device 200 (in relation to the longitudinal axis of the endoscopic anastomosis device 200). In some embodiments, the ends of channels 210a, 210b, and 210c at distal tip portion 202 are curved so as to direct T-fasteners to emerge from endoscopic anastomosis device 200 at a steep angle (e.g., about 45° to about 90°) relative to the walls of esophagus end portion 12a and esophagus end portion 12b. In some embodiments, the ends of channels 210a, 210b, and 210c at distal tip portion 202 are curved so as to direct T-fasteners to emerge from endoscopic anastomosis device 200 essentially perpendicularly relative to the walls of esophagus end portion 12a and esophagus end portion 12b. Such an angle of emergence can help facilitate the T-fasteners to puncture the walls of esophagus end portion 12a and esophagus end portion 12b. In some embodiments, overtubes can be slidably disposed within channels 210a, 210b, and 210c (as in the manner described above in reference to overtube 110 used in conjunction with endoscopic T-fastener tissue closure device 100).

Figure 7:
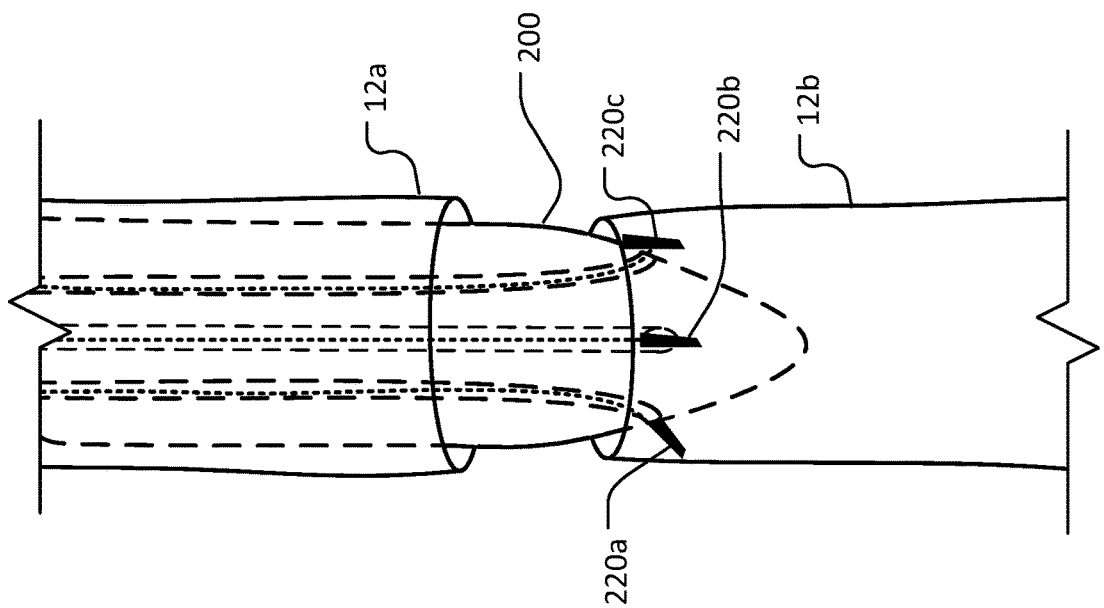

Referring to FIG. 7, with distal tip portion 202 within esophagus end portion 12b, T-fasteners 220a, 220b, and 220c can be pushed to emerge from channels 210a, 210b, and 210c, and to penetrate through esophagus end portion 12b. In some embodiments, T-fasteners 220a, 220b, and 220c have a beveled tip to facilitate penetration through esophagus end portion 12b. In some embodiments, T-fasteners 220a, 220b, and 220c are essentially triangular, with a pointed tip for penetration and a widen base for tissue apposition.

In some embodiments, T-fasteners 220a, 220b, and 220c are pushed to emerge from channels 210a, 210b, and 210c using pusher catheters (not shown). In some embodiments, T-fasteners 220a, 220b, and 220c are pushed to emerge from channels 210a, 210b, and 210c using a lever mechanism as known in the art of endoscopic instruments.

While in the depicted embodiment channels 210a, 210b, and 210c direct T-fasteners 220a, 220b, and 220c to emerge from the tapered leading end of distal tip portion 202, in some embodiments channels 210a, 210b, and 210c are designed differently so as to direct T-fasteners 220a, 220b, and 220c to emerge from a non-tapered portion of distal tip portion 202.

Figure 8:
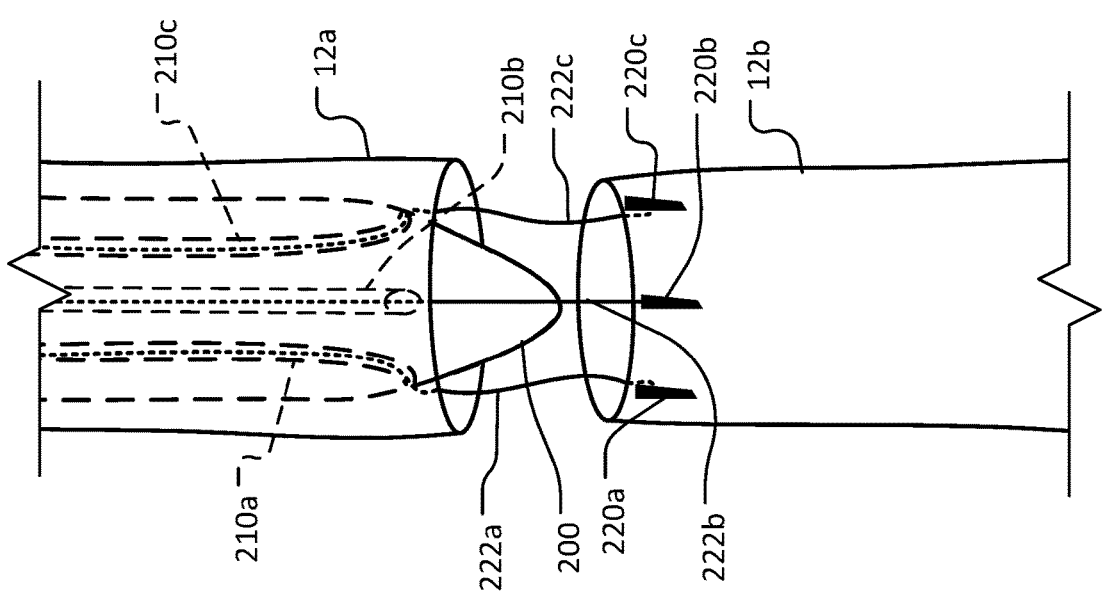

Referring to FIG. 8, after installation of T-fasteners 220a, 220b, and 220c in esophagus end portion 12b, distal tip portion 202 can be pulled back to position it in preparation for installing T-fasteners in esophagus end portion 12a. In this view, sutures 222a, 222b, and 222c that are attached to T-fasteners 220a, 220b, and 220c respectively are clearly in view. In a manner analogous to sutures 122a and 122b described above in reference to endoscopic T-fastener tissue closure device 100, sutures 222a, 222b, and 222c extend from T-fasteners 220a, 220b, and 220c, through endoscopic anastomosis device 200, and terminate at a free ends that are external to patient 10 (i.e., through the mouth).

Figure 9:
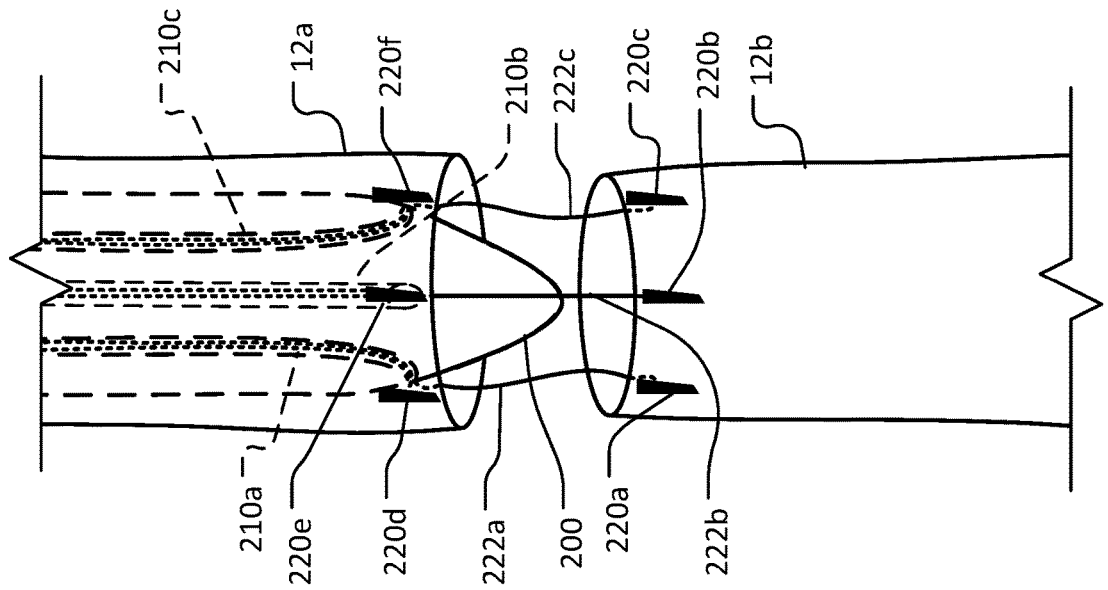

Referring to FIG. 9, with distal tip portion 202 now in position relative to esophagus end portion 12a, T-fasteners 220d, 220e, and 220f can be deployed from endoscopic anastomosis device 200. In the depicted embodiment, T-fasteners 220d, 220e, and 220f are pushed to emerge from channels 210a, 210b, and 210c (the same channels as T-fasteners 220a, 220b, and 220c respectively). Alternatively, in some embodiments T-fasteners 220d, 220e, and 220f can be pushed to emerge from other channels that are adjacent to but distinct from channels 210a, 210b, and 210c.

In some embodiments, T-fasteners 220d, 220e, and 220f are manually loaded into channels 210a, 210b, and 210c after the deployment of T-fasteners 220a, 220b, and 220c. In some embodiments, endoscopic anastomosis device 200 is configured to use a T-fastener cartridge with two or more tranches (groupings) of T-fasteners therein. Accordingly, a first tranche of T-fasteners (e.g., T-fasteners 220a, 220b, and 220c) can be deployed in esophagus end portion 12b, and a second tranche of T-fasteners (e.g., T-fasteners 220d, 220e, and 2200 can be deployed in esophagus end portion 12a.

Referring to FIGS. 10-12, sutures 222d, 222e, and 222f are attached to T-fasteners 220d, 220e, and 220f respectively. After deployment of all T-fasteners 220a, 220b, 220c, 220d, 220e, and 220e, preparations can be made to cinch suture 222a with suture 222d, suture 222b with suture 222e, and suture 222c with suture 222f.

In the depicted implementation, endoscopic anastomosis device 200 is withdrawn prior to cinching the sutures. Thereafter, suture closure clip devices 224a, 224b, and 224c are installed to cinch together T-fastener 220a with T-fastener 220d, T-fastener 220b with T-fastener 220e, and T-fastener 220c with T-fastener 220f. However, in some implementations endoscopic anastomosis device 200 remains in place and suture knots or suture closure clip devices are advanced through channels 210a, 210b, and 210c towards T-fasteners 220a, 220b, 220c, 220d, 220e, and 220e. In any case, sutures knots or suture closure clip devices 224a, 224b, and 224c draw together T-fastener 220a with T-fastener 220d, T-fastener 220b with T-fastener 220e, and T-fastener 220c with T-fastener 220f The drawing together of T-fastener 220a with T-fastener 220d, T-fastener 220b with T-fastener 220e, and T-fastener 220c with T-fastener 220f creates an anastomosis between esophagus end portion 12a and esophagus end portion 12b. Sutures 222a, 222b, 222c, 222d, 222e, and 222f can then be trimmed and the unattached portions can be withdrawn from esophagus 12, along with endoscopic anastomosis device 200 and any other associated instruments.

Figures 13A, 13B:
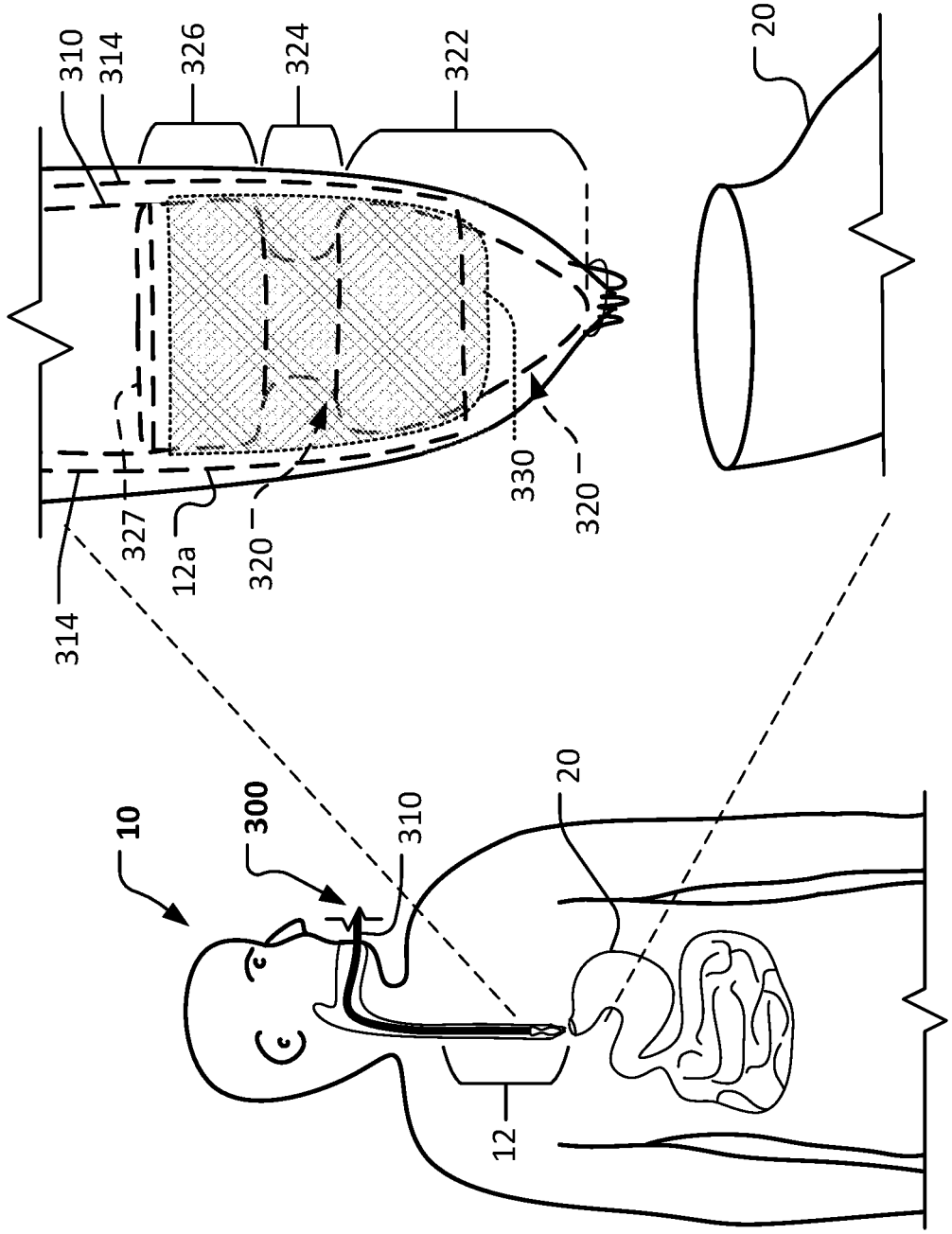
FIGS. 13A and 13B illustrate a patient undergoing another example minimally invasive esophagogastric anastomosis procedure to create a stent-reinforced esophagogastric anastomosis in accordance with some embodiments provided herein.

Referring to the example of FIGS. 13A and 13B, in this depiction patient 10 has had an esophagectomy of the lower esophagus 12. Accordingly, patient 10 is receiving a minimally invasive treatment to create an anastomosis between an esophagus end portion 12a and a stomach 20 using an endoscopic anastomosis device 300 in accordance with some embodiments provided herein. The same devices and techniques described here to create the anastomosis between the esophagus 12 and stomach 12 can be used in other contexts as well. For example, such devices and techniques can be used for scenarios such as, but not limited to, repair of colon resections, anastomosing esophageal portions, gastric bypass, bariatric anastomoses, vascular anastomoses, and the like.

In the depicted embodiment, endoscopic anastomosis device 300 includes a bougie 310, a sheath 314, an obturator 320, and a stent 330. Obturator 320 is releasably attached to the distal end portion of bougie 310. Stent 330 is releasably disposed circumferentially on a portion of obturator 320. Sheath 314 is slidably engaged with bougie 310. A distal end portion of sheath 314 diametrically constrains stent 330 on obturator 320. As described further below, sheath 314 can be pulled proximally in relation to bougie 310 to release stent 330 from being constrained by the distal end portion of sheath 314. In some embodiments, a stent retention member is positioned on bougie 310 and/or obturator 320 that inhibits stent 330 from being displaced proximally as sheath 314 is pulled proximally.

In some embodiments, bougie 310 is a typical flexible, reusable bougie device as is known in the art. In particular embodiments, bougie 310 is a custom device specifically made for use as part of endoscopic anastomosis device 300.

In some embodiments, obturator 320 is threadably attached to bougie 310. In some embodiments, obturator 320 is attached to bougie 310 using another fastening technique such as, but not limited to, using retaining clips, pinning, a bayonet connection, and the like. In some embodiments, obturator 320 is integral with bougie 310, i.e., not releasable.

In the depicted implementation, esophagus end portion 12a has been cinched closed. The closure can be performed using techniques such as, but not limited to, installing one or more sutures (e.g., a purse-string suture, or figure eight suture), a lasso, a clip, and the like. With the esophagus end portion 12a closed as shown, a clinician can maneuver esophagus 12 by manipulating bougie 310 and obturator 320.

In some implementations, obturator 320 may include an extended distal tip (e.g., a rod with a ball at the end, not shown) that becomes captured within the cinched esophagus end portion 12a. In such an arrangement, a clinician may be afforded the capability for even greater maneuverability of esophagus 12 by manipulating bougie 310 and obturator 320. In some implementations, obturator 320 may include a grasping device (not shown). Such a grasping device can be used to releasably capture a portion of esophagus end portion 12a to provide for maneuverability of esophagus 12 by manipulating bougie 310 and obturator 320. In such a case, the need for cinching esophagus end portion 12a may be unnecessary. In still another implementation, obturator 320 may include a lasso device (not shown) that can be reversible deployed to capture esophagus end portion 12a to enable maneuverability of esophagus 12 by manipulating bougie 310 and obturator 320. In yet another implementation, obturator 320 may include one or more barbs (not shown) that can be reversible deployed to capture esophagus end portion 12a to enable maneuverability of esophagus 12 by manipulating bougie 310 and obturator 320.

In the depicted embodiment, obturator 320 includes a tapered distal tip portion 322, a waist portion 324, and a proximal portion 326. In some embodiments, the outer diameter of waist portion 324 is less than the maximum outer diameter of distal tip portion 322 and proximal portion 326. In result, a circumferential open space between stent 330 and obturator 320 exists in the area of waist portion 324.

Obturator 320, or portions thereof, can be made of various types of materials. For example, in some embodiments obturator 320 is made of metallic materials such as, but not limited to, stainless steel, titanium, titanium alloys, and the like. In some embodiments, obturator 320 is made of polymeric materials such as, but not limited to, polypropylene, polysulfone, polyetherimide, polyethersulfone, polyetheretherketone, and the like. In some embodiments, obturator 320 is made of a combination of metallic and polymeric materials.

In some embodiments, obturator 320 is a single use, disposable item. In some embodiments, obturator 320 is a reusable, sterilizable item.

In some embodiments, as in the depicted embodiment, proximal portion 326 may include positional indicator 327. Positional indicator 327 can be used to identify a position and orientation of obturator 320 to a clinician (e.g., a position of waist portion 324 for the placement of T-fasteners, as described further below). In some embodiments, positional indicator 327 is one or more light emitting elements (e.g., LEDs). Such light emitting elements can transilluminate the esophagus (or other body structure) so that the clinician can ascertain the position and orientation of obturator 320. In some embodiments, other types of positional indicators 327 (e.g., radiopaque markers) can be additionally, or alternatively included.

Endoscopic anastomosis device 300 also includes stent 330. As described further below, stent 330 acts as a buttress for the anastomosis. In some embodiments, stent 330 is a bioresorbable, biodegradable, or bioabsorbable stent. In some embodiments, stent 330 is a metallic stent (e.g., stainless steel or nitinol). In particular embodiments, stent 330 may include a graft material that may be biodegradable or durable. Moreover, in various embodiments stent 330 may include an anti-reflux valve (e.g., one-way valve) within the lumen of stent 330. Such a valve may prevent or reduce the likelihood of reflux (e.g., GURD) in some scenarios. In some embodiments, stent 330 may include one or more anchor devices (e.g., hooks, prong, barbs, and the like). Stent 330 is constructed so that T-fasteners can be passed through the wall of stent 330, as described further below.

While stent 330 is depicted as having a certain length, it should be understood that in some embodiments the length of stent 330 is longer or shorter than depicted. For example, in some embodiments stent 330 extends proximally along bougie 310 such that positional indicator 327 is covered by stent 330. It should be understood that stent 330 can be constructed in any suitable fashion such as, but not limited to, expanded material (e.g., a tube that is cut and then expanded), woven strands of material, a fabric, a mesh, and the like. In some embodiments, stent 330 is self-expanding. That is, in some embodiments stent 330 is biased to expand diametrically when the constraint of sheath 314 is removed from stent 330.

Sheath 314 is a flexible tube that is slidably engaged on bougie 310.

Accordingly, a clinician can selectively push and/or pull sheath 314 distally and/or proximally, respectively, in relation to bougie 310 (and in relation to obturator 320 and stent 330). In some embodiments, sheath 314 can be transparent or partially transparent.

A distal end portion of sheath 314 can at least partially encapsulate and thereby protect stent 330 during advancement of endoscopic anastomosis device 300 to a target location within patient 10. Once at the target location, sheath 314 can be pulled proximally to reveal stent 330. In some embodiments, stent 330 is prevented from being displaced proximally as sheath 314 is pulled proximally by a mechanical stopper feature on bougie 310 or obturator 320.

Referring also to FIG. 14, by manipulating bougie 310 (and obturator 320 attached to bougie 310), a clinician can insert esophagus end portion 12a into an opening in the wall of stomach 20 (in this example implementation, or other body structure in other implementations). During this step, sheath 314 can remain in position such that it at least partially encapsulates and protects stent 330.

Referring also to FIG. 15, esophagus end portion 12a is advanced into stomach 20 at least until waist portion 324 of obturator 320 is within stomach 20. In this depiction, stomach 20 is shown in cross-section for better visibility of esophagus end portion 12a within stomach 20.

When endoscopic anastomosis device 300 has been maneuvered to the depicted orientation in relation to esophagus end portion 12a and stomach 20, the clinician can then pull sheath 314 proximally in relation to bougie 310 until stent 330 is fully revealed from within sheath 314. In some cases, stent 330 may self-expand when revealed from the diametrically-constraining confines of sheath 314. In some cases, stent 330 does not self-expand.

Figure 16:
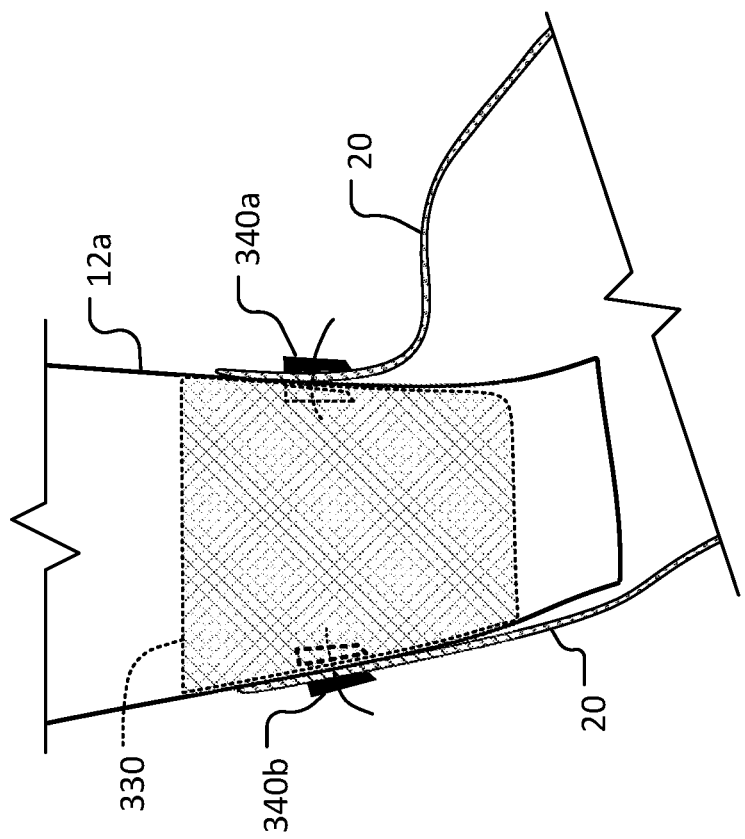

Referring also to FIG. 16, when the clinician has advanced esophagus end portion 12a into stomach 20 to a desired relative position, and sheath 314 has been pulled off of stent 330, a plurality of T-fasteners 340a, 340b, can be installed to create the anastomosis connection between esophagus end portion 12a and stomach 20. While the depiction includes only two T-fasteners 340a, 340b, it should be understood that any number of T-fasteners may be installed as shown around the periphery of the anastomosis (so that a seal is created). In some implementations, positional indicator 327 is used by the clinician as a locational reference for waist portion 324 so that T-fasteners 340a, 340b are installed in waist portion 324. Waist portion 324 provides a relieved area of obturator 320 that physically accommodates the size of T-fasteners 340a, 340b.

Each of the T-fasteners 340a, 340b is installed so that a three-layered wall is created around the periphery of the anastomosis. An innermost wall layer is esophagus end portion 12a. An outer-most wall layer is the wall of stomach 20. The middle layer of the three-layered wall is stent 330. In this arrangement, stent 330 strengthens the anastomosis and helps to facilitate an anastomosis with a complete and durable seal. That said, it should be understood that stent 330 is optional. That is, in some embodiments no stent 330 is used.

Figure 17:
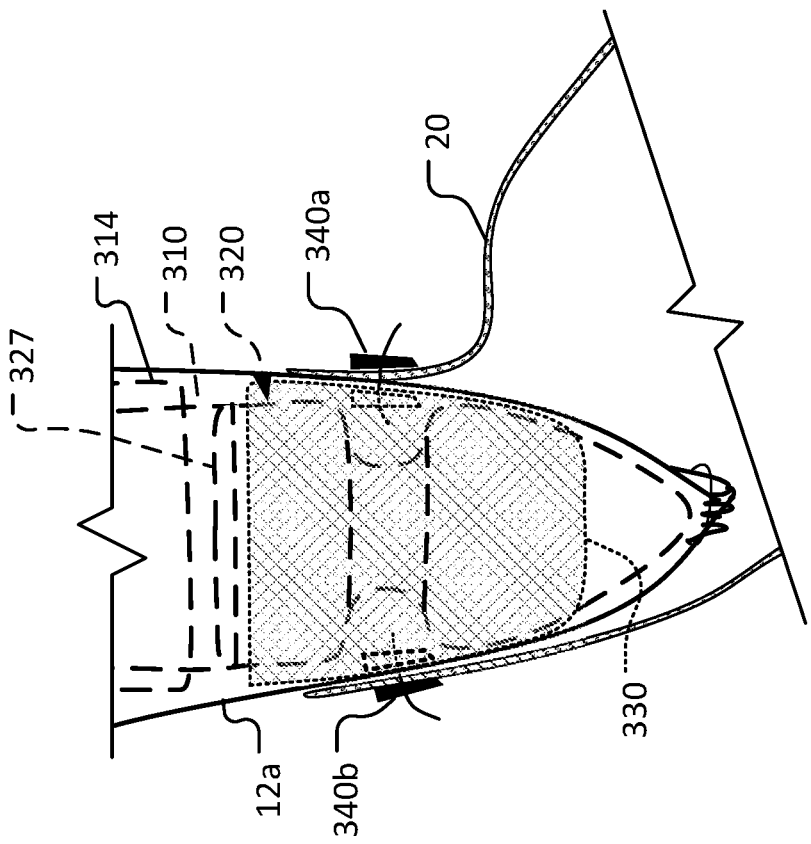

Referring also to FIG. 17, after placement of T-fasteners 340a, 340b, bougie 310 and obturator 320 are removed. Thereafter, the cinch is removed from esophagus end portion 12a. If a suture was used for the cinch, an endoscopic scissors or an argon plasma coagulator can be used to remove the suture, for example. As shown, esophagus 12 is now in open communication with stomach 12.

In some embodiments, stent 330 and/or T-fasteners 340a, 340b are bioresorbable, biodegradable, or bioabsorbable. Hence, after a period of time (such as an amount of time that allows the tissue of esophagus 12 to attach with stomach 12) stent 330 and/or T-fasteners 340a, 340b may deteriorate and be released from the area of the anastomosis. In some embodiments, stent 330 and/or T-fasteners 340a, 340b are not bioresorbable, biodegradable, or bioabsorbable. Hence, after a period of time (such as an amount of time that allows the tissue of esophagus 12 to attach with stomach 12) stent 330 and/or T-fasteners 340a, 340b may be removed via a medical procedure (which may be endoscopic or minimally invasive).

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An endoscopic anastomosis device comprising:
   an endoscope with a plurality of working channels therethrough;
   a plurality of T-fasteners, each T-fastener of the plurality of T-fasteners being slidably disposable within a working channel of the plurality of working channels; and
   a plurality of sutures, wherein each T-fastener of the plurality of T-fasteners has a suture of the plurality of sutures attached thereto,
   wherein a distal end portion of each working channel of the plurality of working channels is configured to direct T-fasteners to emerge laterally from a distal tip portion of the endoscope at an angle from between about 45 degrees to about 90 degrees in relation to a longitudinal axis of the endoscope.

2. The device of claim 1, wherein the distal tip portion of the endoscope comprises a tapered leading end.

3. The device of claim 1, wherein each T-fastener of the plurality of T-fasteners has a beveled tip configured for puncturing tissue.

4. The device of claim 1, wherein the distal tip portion of the endoscope comprises a tapered leading end, and wherein the plurality of working channels have open ends located at the tapered leading end.

5. The device of claim 1, wherein the plurality of working channels comprises three working channels.

6. The device of claim 5, wherein the three working channels are distributed around a circumference of the distal tip portion of the endoscope.

7. The device of claim 1, wherein the plurality of working channels comprises ten working channels.

8. The device of claim 7, wherein the ten working channels are distributed around a circumference of the distal tip portion of the endoscope in even angular increments.

9. The device of claim 1, wherein the plurality of working channels comprises six working channels.

10. The device of claim 9, wherein the six working channels are distributed around a circumference of the distal tip portion of the endoscope in even angular increments.

11. The device of claim 1, wherein the plurality of working channels have end portions that are curved.

\* \* \* \* \*